United States Patent [19]

Sugasawa et al.

[11] Patent Number: 4,551,554
[45] Date of Patent: Nov. 5, 1985

[54] PROCESS FOR PRODUCTION OF 2-HALOACETYLPHENOLS

[75] Inventors: Tsutomu Sugasawa, Kobe; Tatsuo Toyoda, Osaka; Kazuyuki Sasakura, Omihachiman, all of Japan

[73] Assignee: Shionogi & Co., Ltd., Osaka, Japan

[21] Appl. No.: 305,621

[22] PCT Filed: Jan. 16, 1981

[86] PCT No.: PCT/JP81/00012

§ 371 Date: Sep. 23, 1981

§ 102(e) Date: Sep. 23, 1981

[87] PCT Pub. No.: WO81/02157

PCT Pub. Date: Aug. 6, 1981

[30] Foreign Application Priority Data

Jan. 23, 1980 [JP] Japan ................................ 55-7148

[51] Int. Cl.$^4$ ............................................. C07C 45/46
[52] U.S. Cl. ................................................. 568/322
[58] Field of Search ............................. 568/308, 322

[56] References Cited

PUBLICATIONS

Ruske, Friedel Crafts & Related Reactions, vol. III, pp. 403–410, 416–419, 439, 450, (1963).
Sugasawa et al., J. Org. Chem., vol. 44, #4, pp. 578–586, (1979).
Booth et al., J.C.S. Perkin Tran. I, pp. 2894–2900, (1980).

Primary Examiner—James H. Reamer
Attorney, Agent, or Firm—Wenderoth, Lind & Ponack

[57] ABSTRACT

A new process for production of 2-haloacetylphenols having the general formula

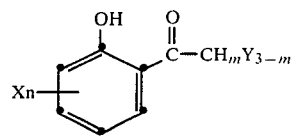

(wherein,
Y is halogen atom;
m is an integer of 0–2,
X and n have the same meaning as mentioned below),
which comprises reacting phenols having the general formula

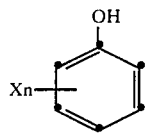

(wherein,
X is hydrogen, $C_1$–$C_5$alkyl, $C_3$–$C_6$cycloalkyl, $C_1$–$C_5$alkoxy or halogen atom;
n is an integer of 0–2)
with haloacetonitriles and boron halide compounds in the presence of condensing coagents.

1 Claim, No Drawings

PROCESS FOR PRODUCTION OF 2-HALOACETYLPHENOLS

The present invention relates to a new process for production of 2-haloacetylphenols.

BACKGROUND ART

The objective compounds in the present invention, 2-haloacetylphenols (I) are important as intermediates in preparation of drugs, agricultural chemicals, perfumes, dyes, etc. A sufficient process for production thereof, however, has not been established. In the prior art, the Friedel-Crafts reaction of phenols (II) and the Fries rearrangement of haloacetoxybenzenes (III) have been utilized. These reactions, however, have the common disadvantage that the substitution occurs at both ortho and para position and moreover the para-substituted compounds (IV) are the main products.

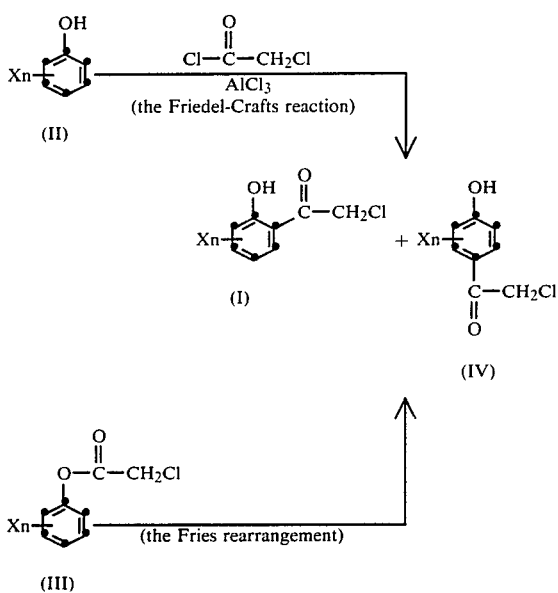

DISCLOSURE OF INVENTION

The present invention relates to a new process for production of 2-haloacetylphenols, which comprises reacting phenols having the general formula

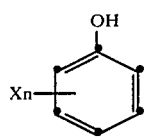

(wherein,
X is hydrogen, $C_1$-$C_5$alkyl, $C_3$-$C_6$cycloalkyl, $C_1$-$C_5$alkoxy or halogen atom and;
n is an integer of 0-2)
with haloacetonitriles having the general formula $$CN-CH_mY_{3-m} \quad (V)$$

(wherein,
Y is halogen atom and;
m is an integer of 0-2)
and boron halide compounds having the general formula

(wherein,
R is halogen atom and;
R' is halogen atom, $C_1$-$C_5$alkyl or $C_6$-$C_{10}$aryl)
in the presence of condensing coagents to give the compounds having the general formula

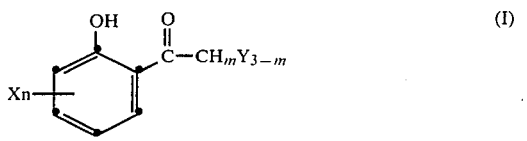

(wherein, X, Y, m and m each has the same meaning as mentioned above).

The following are explanations of the terms used in the above definition:

$C_1$-$C_5$alkyl; methyl, ethyl, propyl, isopropyl, butyl, isobutyl, sec-butyl, t-butyl, pentyl, etc.

$C_3$-$C_6$cycloalkyl; cyclopropyl, cyclopentyl, cyclohexyl, etc.

$C_1$-$C_5$alkoxy; methoxy, ethoxy, propoxy, isopropoxy, butoxy, isobutoxy, pentyloxy, etc.

$C_6$-$C_{10}$aryl; phenyl, tolyl, xylyl, naphthyl, etc.

As halogen atom, fluoro, chloro, bromo, iodo, etc. are mentioned.

The halogen atoms in boron halide compounds (VI), however, mean chloro and bromo, particularly chloro is preferred.

This reaction may be conducted in the presence of condensing coagents in a suitable inert solvent at a temperature of 0°–150° C., preferably at room temperature or under heating at approximately the boiling point of the solvent employed. As a condensing coagent, Lewis acids such as aluminum chloride, zinc chloride, titanium tetrachloride, tin tetrachloride, ferric chloride, etc. are exemplified, particularly aluminum chloride is preferred. As a solvent, methylene chloride, 1,2-dichloroethane, benzene, toluene, xylene, etc. are employed. The condensing coagents may be used in an amount of about 0.1–1.5 mole, preferably about 0.1–0.5 mole, per 1 mole of the starting phenol.

The starting phenols (II) may have the same or different kind of 1-2 substituents selected from alkyl, cycloalkyl, alkoxy, and halogen atom on the benzene ring. At least one site of the ortho-positions of the benzene ring, however, must be vacant in order that the reaction occurs. Practically, phenol, alkylphenol, cycloalkylphenol, alkoxyphenol, halophenol, 2,3-dihalophenol, 2,4-dialkylphenol, 3-cycloalkyl-4-halophenol, etc. are mentioned.

And as haloacetonitriles (V), monohaloacetonitrile (chloroacetonitrile, bromoacetonitrile, iodoacetonitrile, etc.), dihaloacetonitrile (dichloroacetonitrile, dibromoacetonitrile, etc.) and trihaloacetonitrile (trichloroacetonitrile, etc.) are mentioned.

As boron halide compounds (IV), boron trihalide such as boron trichloride and boron tribromide, and hydrocarbon boron dihalide such as butylboron dichloride, phenylboron dichloride and phenylboron dibromide are mentioned, particularly boron trichloride is preferred.

Haloacetonitriles (V) and boron halide compounds (VI) may be used in an amount of about 1.0–1.2 mole preferably about 1.0–1.1 mole per 1 mole of the starting phenol.

CAPABILITY OF EXPLOITATION IN INDUSTRY

The resulting objective compounds (I) in the present invention are useful as raw materials for drugs, agricultural chemicals, perfumes, dyes, etc. For example, 4-chloro-2-(2-chloroacetyl)-5-cyclohexylphenol is treated with sodium acetate to cyclize, and reduced with sodium borohydride, in order to convert the oxo group to the hydroxy group, followed by catalytic hydrogenation with palladium/carbon in hydrogen atomosphere, eliminating the hydroxy group to give 5-chloro-6-cyclohexyl-2,3-dihydrobenzofuran having analgesic and anti-inflammatory effects.

(i) $CH_3COONa$
(ii) $NaBH_4$
(iii) $Pd-C/H_2$ (Germ. Offen. 2,803,544)

BEST MODE IN PRACTICING INVENTION

The following explain the mode of practicing the present invention.

EXAMPLE 1

To a solution of boron trichloride (696 mg, 6 mmol) in 1,2-dichloroethane (3 ml) under cooling are added a solution of phenol (475 mg, 5 mmol) in 1,2-dichloroethane (5 ml), chloroacetonitrile (0.38 ml, 6 mmol) and aluminum chloride (800 mg, 6 mmol), successively and the resulting mixture is refluxed under heating for 6 hours. After cooling, ice water is added to the reaction mixture, stirred for 30 minutes at room temperature, and extracted with methylene chloride. The organic layer is chromatographed on a silica gel column and the benzene eluate is evaporated to give 2-(2-chloroacetyl)-phenol (672 mg).

Yield: 78.8%. Recovery of phenol: 69 mg (14.5%).

EXAMPLE 2

In the manner of the aforementioned Example 1, the reaction is carried out in the presence of 0.5 equimolar amount of aluminum chloride at room temperature in methylene chloride as a solvent to give 2-(2-chloroacetyl)phenol in 85.7% yield.

EXAMPLE 3

Phenylboron dichloride instead of boron trichloride is employed and worked up in the same manner as in Example 1 mentioned above to give 2-(2-chloroacetyl)-phenol in 64.6% yield.

EXAMPLE 4

To a solution of boron trichloride (394 mg, 3.9 mmol) in 1,2-dichloroethane (3.6 ml) under cooling are added a solution of o-cresol (386 mg, 3.6 mmol) in 1,2-dichloroethane (4 ml), chloroacetonitrile (0.25 ml, 3.9 mmol) and aluminum chloride (240 mg, 1.8 mmol), and the mixture is stirred at room temperature for 20 hours. The reaction mixture is worked up in the same manner as in Example 1 to give 2-(2-chloroacetyl)-6-methylphenol (499 mg).

Yield: 75.0%. mp 65°–66° C. (Reference quoted 67° C.; Anwers, Ber., 49, 812 (1916)).

IR, $\nu_{max}^{CHCl_3}$: ~3010, 1640 cm$^{-1}$

NMR, $\delta^{CDCl_3}$: 2.24(3H, s., $CH_3$), 4.69(2H,s., $\underline{CH_2}CO$), 6.80 (1H,t., J=8 Hz, 4-H), 7.45(2H,dd, J=8 Hz, J=2 Hz, 3-H, 5-H), 11.98(1H,s., O$\underline{H}$)

Elementary analysis $C_9H_9ClO_2$: Calcd. C,58.55; H,4.91; Cl,19.21 (%), Found (C,58.79; H,4.89; Cl,19.07 (%).

Recovery of o-cresol = 15%

EXAMPLE 5–10

The following phenols (II) are treated in the same manner as in Example 4 to give the corresponding objective compounds (I)

| Example No. | II Xn | I Xn | mp (°C.) | Yield (%) | Recovery of Phenol (%) |
|---|---|---|---|---|---|
| 5 | 2-Cl | 6-Cl | 72–73 | 10.9* | 47.7 |
| 6 | 3-Cl | 5-Cl | 75–76 | 51.4 | 44.3 |
| 7 | 4-Cl | 4-Cl | 65–66** | 17.9 | 76.3 |
| 8 | 2-OCH$_3$ | 6-OCH$_3$ | 113–114 | 42.4 | 15.0 |
| 9 | 3-OCH$_3$ | 5-OCH$_3$ | 117–118 | 80.7 | — |
| 10 | 4-OCH$_3$ | 4-OCH$_3$ | 83–84 | 67.4 | 26.1 |
| 11 | 2-CH$_3$, 3-CH$_3$ | 5-CH$_3$, 6-CH$_3$ | 95–96 | 100 | 0 |

Note:
*After reaction for 7 days, the yield rises to 21.3%.
**Reference quoted mp 65° C. (Ranisteano et al., Chem. Abst., 72, 12783g (1972)).

EXAMPLE 12

Phenol instead of o-cresol and trichloroacetonitrile instead of chloroacetonitrile are employed and worked up in the same manner as in Example 4 to give 2-(2-trichloroacetyl)phenol as an oily substance in 91.9% yield.

NMR, $\delta^{CDCl_3}$: 6.8–7.6 (3H,m, aromatic H), 8.2(1H,dd, J=8 Hz, J=2Hz, 6-H), 11.1(1H,s., O$\underline{H}$)

We claim:
1. A process for production of 2-haloacetylphenols which comprises reacting a phenol having the formula

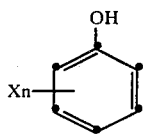

wherein,
X is hydrogen, $C_1$–$C_5$ alkyl, $C_3$–$C_6$ cycloalkyl, $C_1$–$C_5$ alkoxy or a halogen atom, and
n is an integer of 0–2
with a haloacetonitrile having the formula $$CN-CH_mY_{3-m}$$

wherein,
Y is chlorine or bromine and
m is an integer of 0–2
and a boron halide compound having the formula

wherein,
R is chlorine or bromine, and
R' is chlorine, bromine, $C_1$–$C_5$ alkyl or phenyl
in the presence of a Lewis acid to give a compound having the formula

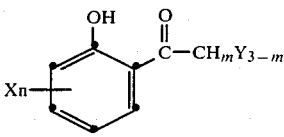

wherein, X, Y, m and n are as defined above.

* * * * *